United States Patent [19]

Krongauz et al.

[11] Patent Number: 4,927,917
[45] Date of Patent: May 22, 1990

[54] QUASI-LIQUID CRYSTALS

[75] Inventors: Valeri A. Krongauz; Felix P. Shvartsman, Rehovot, Israel

[73] Assignee: Yeda Research and Development Co., Ltd., Rehovot, Israel

[21] Appl. No.: 287,501

[22] Filed: Dec. 19, 1988

Related U.S. Application Data

[63] Continuation of Ser. No. 659,819, Oct. 10, 1984, abandoned.

[30] Foreign Application Priority Data

Oct. 10, 1983 [IL] Israel ......................................... 69939

[51] Int. Cl.$^5$ ..................... G02B 5/23; C09K 19/34; C09K 19/54; C07D 491/107
[52] U.S. Cl. ..................... 534/567; 534/577; 534/611; 534/752; 534/787; 548/409; 548/411; 252/299.01; 252/299.61; 252/586
[58] Field of Search .............. 252/586, 299.01, 299.61; 548/409, 411; 534/577, 611, 752, 567

[56] References Cited

U.S. PATENT DOCUMENTS

| | | | |
|---|---|---|---|
| 3,501,410 | 5/1970 | Newland et al. | 252/586 |
| 3,884,697 | 5/1975 | Inoue et al. | 252/586 |
| 4,003,633 | 1/1977 | Yamashita | 252/299.01 |
| 4,116,862 | 9/1978 | Wippler | 252/586 |
| 4,405,733 | 9/1984 | Williams et al. | 430/345 |
| 4,556,605 | 12/1985 | Mogami et al. | 252/556 |

FOREIGN PATENT DOCUMENTS 58-113203 7/1983 Japan ............................ 252/299.61

OTHER PUBLICATIONS

Schnuriger et al, CA 86:88850, (1977).
Kobayashi, CA 92:197581, (1980).
Otkuba et al., CA 97:23011, (1982).
"Quasi-Liquid Crystals", By: Felix Shvartsman et al, reprinted from *Nature*, vol. 309, No. 5969, pp. 608-611, June 14, 1984.
"Quasi-Crystals, Growth from Photochromic Spiropyrans on Irridation in a Constant Electric Field", By: V. A. Krongauz et al, Reprinted from *The Journal of Physical Chemistry*, vol. 82, No. 23, 1978.
"Investigation of the Quasi-Liquid Crystal Structure", By: Felix P. Shvartsman et al, Reprinted from *The Journal of Physical Chemistry*, 1985, 89, 3941–3946.

*Primary Examiner*—Howard J. Locker
*Assistant Examiner*—J. E. Thomas
*Attorney, Agent, or Firm*—Browdy and Neimark

[57] ABSTRACT

There are provided compounds which give quasi-liquid crystals, which comprise a mesogenic group, which can contain bridging groups, a bridging group and a spiropyran moiety having a 2H pyran ring, a terminal group being attached to the mesogenic group. The mesogenic group contains two aromatic, heterocyclic or cycloaliphatic ring structures. The compounds are prepared by a coupling reaction of mesogenic groups with a spiropyran compound via a suitable bridging group. There is provided a process for producing quasi-liquid crystalline (QLC) films which are useful for producing a wide variety of devices based on the optical non-linearity of generation of second harmonics by such films. Such devices can also be based on ferroelectric, pyroelectric, piezoelectric effects and photoactivity of such oriented QLC films.

5 Claims, 2 Drawing Sheets

QUASI-LIQUID CRYSTALS

This application is a continuation, of application Ser. No. 659,819, filed 10/10/84, now abandoned.

FIELD OF THE INVENTION

There are provided compounds containing spiropyran and mesogenic moieties and a process for the production of such compounds.

There are provided orientated quasi-crystalline films produced from such compounds, based on the partial thermoconversion of the spiropyran into the merocyanine form and stabilization of the quasi-liquid crystalline state by the application of a suitable electrostatic field, resulting in an alignment of the film. The films thus obtained can be used in a wide variety of devices employing second harmonics or other non-linear optical effects.

BACKGROUND OF THE INVENTION

The following U.S. Patents and publication in scientific literature are of relevance to the subject matter of the present invention:

3,922,485-11/1975 Starkweather et al. 178/7.6
4,040,096-8/1977 Starkweather 358/302
4,405,733-9/1983 Williams et al. 430/345

D. Chemla, J. L. Oudar and J. Zyss, L'Echo des Rescherches (Intern. issue) 47, (1981).

D. J. Williams, Ed. Non linear Optical Properties of Organic and Polymeric Materials, ACS Publish, (1983).

A. Dulcic and C. Flytzanis. Opt. Com. 25, 402 (1978).

G. R. Meredith, V. A. Krongauz and D. J. Williams. Chem. Phys. Lett., 87, 289 (1982).

F. P. Shvartsman and V. A. Krongauz. Nature, 309, 608–611 (1984).

H. Kelker and R. Hatz. Handbook of Liquid Crystals, Chemie, Weinheim, (1980).

Gale, D. J. Wilshire, J. F. K., J. Soc. Dyers Colour 90, 97 (1974).

Tarbell, D. S. Yamomoto, Y., Pope, B. M., Procl. Natl. Acad, Sci., USA 69, 730 (1972).

Itoh, M., Hagiwara, D., Kamiya, T., Bull Chem. Soc. Jpn. 50, 718, (1977).

Hinnen, A., Audic, C., Gautron, R., Bull. Soc. Chim. France, 5, 2066, (1968).

Lundt, B. F., Johansen, N. L., Volund, A., Makussen, J., Int. J. Pept. Protein Res., 12, 258, (1978).

Hassner, A., Alexanian, V., Tetrahedron Letters, 46, 4475, (1978).

Orahovats, A. S., Radeva, T. Zh., Spassov, S. L., Comp. Rend. Acad. Bulg. Sci., 26(5), 663, (1973).

When light is propogated through an optical dense medium, the induced electronic polarization of the material in an electric field E can be represented by the following expression:

$$P = \chi^{(1)}E + \chi^{(2)}E^2 + \chi^{(3)}E^3 + $$

$$P = P_1 + P_2 + P_3 + $$

where the $\chi$'s are coefficients of successive powers of the field, and $\chi^{(n)}$ is usually about $10^5 \chi^{(n+1)}$. This means that the high order terms will be important only at very high fields. $P_1$ is the linear polarization and $P_2$ is the first non-linear polarization. Symmetry considerations require that $P_2 = 0$ if the material has a center of symmetry associated with it. Finite values of $P_2$ gives rise to new phenomena with considerable practical importance in laser-related technologies, optical communications and information processing (D. Chemla, J. H. Oudar and J. Zyss, L'Echo des Recherches (Intern. issue) 47, (1981). Materials with high second-order non-linear properties ($\chi^{(2)} >> 0$) are generally based on molecules having high first hyperpolarizabilities. Originally only inorganic crystals were used in optical devices based on these properties. However, recent research has led to the discovery of some organic crystals which have second-order non-linear optical coefficients several orders of magnitude larger than those of the conventional inorganic ones, and with much larger damage thresholds (D. J. Williams, ed., Nonlinear Optical Properties of Organic and Polymeric Materials, ACS Publish., 1983).

One example is 2-methyl-4-nitroaniline crystals with $\chi^{(2)} = 1.25 \times 10^{-6}$esu. However, it is difficult to grow single crystals of this material of good quality, and not feasible to prepare thin films.

Recently it was shown that the molecular hyperpolarizability of some merocyanine dyes is surprisingly high (A. Dulcic and C. Flytzanis, Opt. Com. 25, 402 1978). If one uses this value and assumes that the merocyanine molecules are aligned in the bulk phase such that the material is noncentrosymmetric and that all of the molecular dipoles point in the same direction, $\chi^{(2)}$ would be approximately $10^{-5}$esu. This would be the largest known value for nonlinear optical material and would enable the use of these materials in a variety of practical devices.

One of the most useful effects for investigation of optical non-linearity of material is second harmonic generation, SHG, which manifests itself as the conversion of light frequency $2\epsilon$ on propagation through a suitable material.

There is known an electro-optical modulator, containing usually Pockel's cell which can be used in scanning devices. Such a device can transfer video information to a scanned medium by a scanning system, see for example, U.S. Pat. Nos. 3,922,485 and 4,040,096. The materials which may be used in such electro-optical modulators include crystals of $KHPO_4$, $LiTaO_3$, $LiNbO_3$, BSN, etc. The property of these materials which make them useful in a device such as the Pockel's cell is their first non-linear polarization.

SUMMARY OF THE INVENTION

The invention relates to novel spiropyran-merocyanine compounds, containing mesogenic groups, which compounds are of the general formula

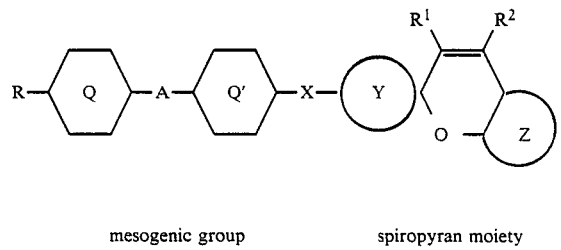

mesogenic group      spiropyran moiety and which compounds comprise a mesogenic group, a bridging group X, a spiropyran moiety and a terminal group R, as marked in the above formula, and wherein the mesogenic group may contain bridging groups A, wherein the spiropyran moiety comprises a 2H pyran ring, the 2-carbon of which is involved in a spiro linkage and a group Y and a cyclic moiety Z, each of which is an aromatic, heteroaromatic or cycloaliphatic ring or ring system, which ring or rings may bear non-interfering substitutes, wherein the ring structures Q and Q' of the mesogenic group are aromatic, heterocyclic or cycloaliphatic moieties, said bridging groups X and A being selected from —HC=N—, —ON=N—, —N=N—, —OC—O—, —C≡C—, —CH=CH—, —OC—NH—, —CH$_2$—CH=N—, —CH=CH—OC—O, —CH=N—N=CH—, —OOC—(CH$_2$)$_n$—COO—, —N=C=N—, —CH=CH—OC—, —CH=N—NH—, —CH=CH—CH=CH—, —O—(CH$_2$)$_n$—O— —N=CH—CH=N—, —NH—(CH$_2$)n—NH— —OC—O—N=CH—, or —CH$_2$—NH—, —CH$_2$O—, —(CH$_2$)$_n$— —(CH$_2$)$_n$—COO—; the terminal group R being selected from —OR', —R', —COOR', —OOCR', —OOCOR', —CN, —Cl, —NO$_2$, —COR', —CH=CH—COOR', —F, —Br, —I, —NC, —NC=O—, —N=C=S, —N$_3$, —R", —OH, —OR", —COOR", —OCR", —NH$_2$, —NHR", —NR"$_2$, wherein —R' is straight chain alkyl and wherein R" is branched alkyl or alkenyl, and wherein R$^1$ and R$^2$ are alkyl and n is an integer.

Preferred groups Q and Q' are phenyl, biphenyl, substituted phenyl, substituted biphenylene, 5- or 6-membered heterocyclic rings with one or more nitrogen, oxygen or sulfur atoms and cycloaliphatic rings. There are known a multitude of mesogenic moieties from literature and essentially all of these are suitable for coupling with the spiropyran moiety to result in compounds of use for the purpose of the present invention.

The invention further relates to a process for the preparation of compounds of the type defined above, and to the production from such compounds of aligned quasi-liquid crystalline films which are useful in a variety of electro-optic devices. The main object of the present invention is to provide a novel product, provided in the form of the oriented quasi-liquid crystalline thin film having exceptional non-linear optical properties, which make possible a variety of applications.

The novel materials exhibit some features of liquid crystals (birefringence, orientation in an electric field), but have different structures. It is suggested to call them "quasi-liquid crystals" (QLC) (Shvartsman, F. P. and Krongauz, V. A., Nature, 309, 608,611, (1984). The spiropyrans of the general formula as hereinbefore defined, are thermo- and photo-chromic in solution.

Yellow crystals of these compounds, obtained by slow crystallization from suitable solvents, have sharp melting points (Table 3) and give green or greenish-blue isotropic melts. The change in color on melting is associated with a shift of the thermal equilibrium (eq 1) to the right. The thin amorphous films of spiropyrans obtained as described above also change their color on heating. The relatively slow rate of transformation of the metastable films is associated apparently with the presence, at low concentrations, or merocyanine molecules, even at room temperature. The merocyanine acts as an impurity, retarding crystallization of the films. On heating, the amorphous films give the anisotropic structures observable under the polarization microscope through their birefringence textures. The appearance of this texture coincides with a substantial change in the film color, from yellow to bright green or greenish-blue. At a still higher temperature, this texture disappears: above this clearing point total extinction of light is observed through cross polarizers.

The temperature range in which the textured structure exists is much lower than the melting point of the crystals. For example, for spiropyran, [V], with R=CH$_3$O—, the mp is 198°-203° C., while the temperature range for the birefringent texture is 50°-130° C. The material above 130° C. is an isotropic liquid which is metastable above the melting point of the crystal. The texture, which disappears above 130° C., reappears on cooling below 130° C. However, this process is not completely reversible due to the competitive crystallization process, which is slow at low temperatures but proceeds faster at higher temperatures. It looks as if the mesophase is "hidden" beneath the crystal phase and appears when we destroy the crystal lattice by dissolving the crystalline spiropyrans. However, this is not the case because the isotropic material obtained by heating spiropyran crystals above the melting point gives, on cooling, isotropic glass, which does not exhibit birefringence on being reheated from room temperature, i.e. the system does not exhibit properties of a monotropic mesophase.

Orientation of the QLC occurs when the films are placed in a constant electric field or more than 0.5 kV/mm as described in the Experimental Section. For example, films of compounds [VI] with R=n—C$_6$H$_{13}$O— at 100° C. and E=1.5 kV/mm gave nearly homogenous birefringence and uniaxial alignment expanded from electrodes during 20–30 sec. after evaporation of the solvent (FIG. 1). Dichroic contrast due to merocyanine alignment was observed when the film was viewed with a single polarizer, perpendicular and parallel to the applied field. The higher the field and the temperature (below the clearing point) the better and more uniform was the orientation. Orientation does not occur in an electric field at temperatures above the clearing point, but does when the film is cooled below this temperature in the field. Orientation in an electrostatic field was observed also on the hydrophobic surface obtained by treating the slide with a solution of octadecyltrichlorosilane in bicyclohexyl. The most remarkable effect of the electrostatic field is the stabilization of the quasi-liquid crystalline state which accompanies the orientation of the films. Spontaneous crystallization no longer occurs. In the supercooled conditions at room temperature the orientation and glass-like state were preserved without change for at least one year after the field was switched off. Both scanning electron microscope and optical microscope observations showed the absence of crystals. The extinction coefficient of merocyanines in the visible absorption maxima ($\Sigma$ mer) obtained from different spiropyrans lie in the rather narrow range $(3-5) \times 10^4 \times \text{liter} \times \text{mole}^{-1} \times \text{cm}^{-1}$. Assuming these coefficients to be valid for the films, and knowing the extinction coefficients of the spiropyrans, we can estimate the ratio of the concentrations of merocyanine and spiropyran in these films from the absorption spectra (FIG. 2):

Cmer/Csp=($\epsilon$sp/$\epsilon$mer)×(Dmer/Dsp), where Dmer and Dsp are the absorbances of merocyanine and spiropyran, respectively. The estimate is that the extent of conversion of spiropyran into merocyanine for most films is only 3–10%. A further most surprising fact, is that the absorption spectra of the films are dichroic only in the region of the merocyanine absorption band ($\lambda$ max approximately 600 nm), while in the region of spiropyran absorption band ($\lambda$ max approximately 370 nm) the degree of linear dichroism is vanishingly small. This means that only the merocyanine molecules are aligned in the electric field, while the bulk of the material, which consists of spiropyran molecules, is unaligned. The order parameter of the merocyanines is given by $S=(D_\parallel - D_\perp)/(2D_\perp + D_\parallel)$, where $D_\parallel$ and $D_\perp$ are, respectively, the absorption parallel and perpendicular to the electeric field. This parameter depends on the field strength, the temperature and the film thickness. Under optimum conditions the order parameter is $S=0.4$. The direction of the long molecular axis, coincident with the direction of maximum absorption of polarized light, is parallel to the field for all examined compounds and mixtures. Measurements of the linear dichroism of orientated QLC films were also carried out in the presence of the dye additives 4-dimethylamino-4'-nitrostilbene (DANS) and 1,6-diphenylhexatriene (DPH). This allowed us to estimate the order parameters of the merocyanines (FIG. 2).

Simple considerations lead to the conclusion that orientation of separate merocyanine molecules is inconceivable in an electric field as weak as 1–1.5 kV/mm. Only assemblies of the interacting molecules, having large dipole moments, can be orientated in such a field. It is also inconceivable that weak interactions, determined by the anisotropy of the molecular polarizabilities of mesogenic groups and responsible for the occurrence of the liquid crystalline state of material, would keep together the merocyanine molecules in such assemblies. Indeed, the concentration of merocyanines in the isotropic bulk is low (3–10%) and the intense birefringence of the QLC, which indicates ordering of the material, the characteristic temperature behaviour and the response to an electric field, all characterize the bulk material as a nematic mesophase. Lack of uniaxial alignment of the spyropyrans in the field impede formation of a regular nematic structure by the mesogenic groups. One may suggest that the spiropyrans form domains with a structure similar to that of the axially symmetric micelles in liotropic liquid crystals located closely and interacting with each other.

The fact that QLC appear only in films cast from solution and never from spiropyran melt, may indicate some latent preorganization or aggregation developing on evaporation of solvent.

The novel quasi-liquid crystals are organized in polar structures, and thus exhibit non-linear optical properties. Indeed, experiments on the SHG from thin films of this material showed a very high efficiency of optical frequency-doubling.

The following are some of the many possible applications of the novel quasi-liquid crystalline films:

Non-linear optics: Hyperpolarizability of mero-cyanine molecules and their complexes, uniform orientation on a molecular level, degree of orientation and optical transparency of quasi-liquid crystalline films are more pronounced, in QLC films than in the known quasi-crystals (Meredith, G. R., Krongauz, V. A., and Williams, D. J., Chem. Phys. Lett., 87, 289,294 (1982), U.S. Pat. No. 4,405,733. This determines non-linear optical effects and related applications, such as: second harmonic generation (frequency doubling)—useful in frequency conversion for near IR solid state lasers and frequency mixing—useful in parametric amplification, infrared up conversion and optical gating; Pockels anisotropy—useful in variable retardation, Q-switch, pulse, and extractors (shutters); electro-optic effect—useful in modulators and detectors; and optical rectification—useful to achieve optical bistability.

Ferroelectrics: Due to the high permanent dipole moment of the merocyanine, certain QLC's exhibit fero-electric properties. Applications include information storage, displays and capacitors.

Pyroelectrics: Changes in the separation of centers of positive and negative change caused by temperature changes can be utilized in the construction of thermal detectors.

Piezoelectrics: A relationship exists between the change in the separation of the centers of positive and negative charge and expansion or contraction of the QLC. Uses of this effect include microphones, headphones, phonograph cartridges and ultrasonic cleaners, etc.

Photoconductors: QLC's may be used in devices based on photoconductivity and photovoltaic effect, such as electrophotography devices, photodetectors and devices for solar energy conversion.

Substrates upon which QLC films of the present invention may be cast include glass, silicone or polymeric support material.

DESCRIPTION OF THE PREFERRED EMBODIMENT

Figures 1A, 1B:
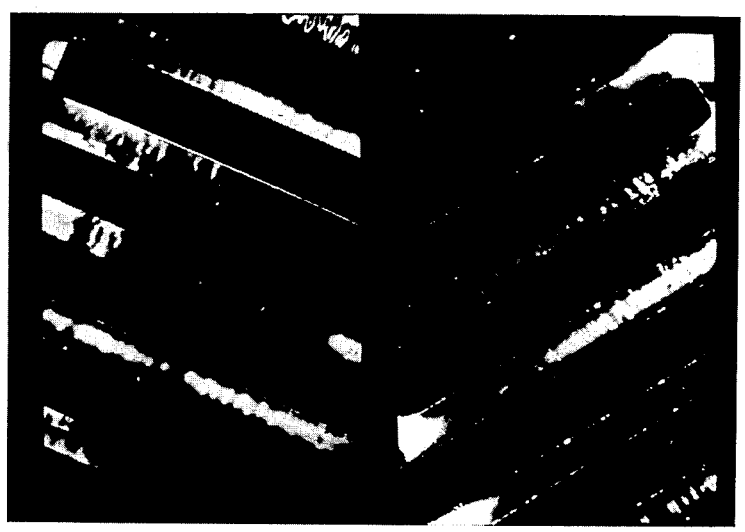
FIG. 1 shows the optical texture of QLC film, prepared from spiropyran [VI] with $R=n-C_6H_{13}O-$ and aligned in electrostatic field ($E=1.5$ kV/mm, at 100° C., distance between electrodes-11 mm), viewed through crossed polarizers, when light is polarized parallel (a) and perpendicular (b) to the long molecular axis. The black parallel strips on the picture are areas of the interdigital electrodes.
Figure 2:
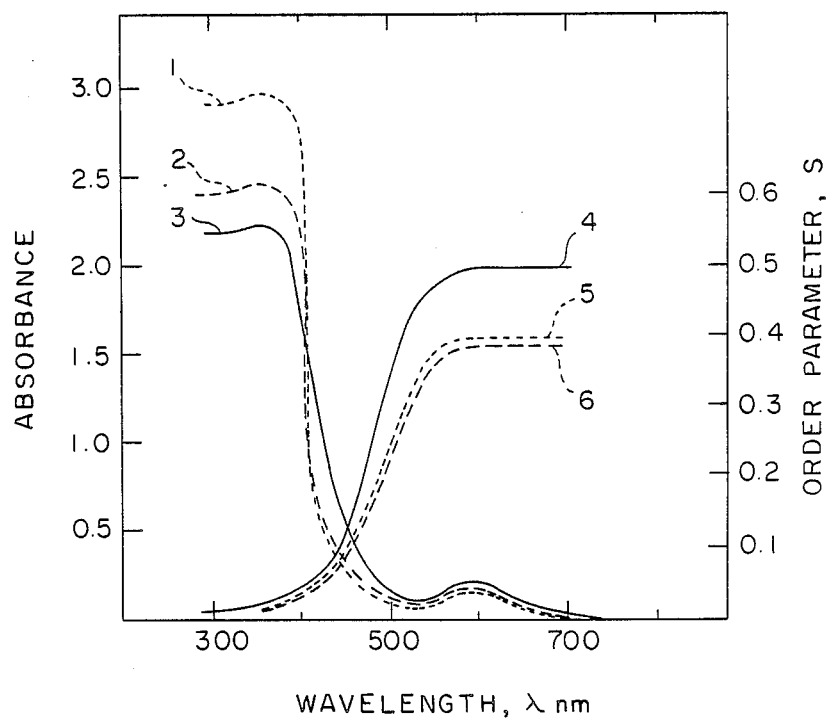
FIG. 2 shows the absorption spectra (1–3) and order parameter S (4–6) of orientated QLC films; 1,5-mixture of spiropyrans [V] which $R=CH_3O-$ and [VI] with $R=n-C_6H_{13}O-$ in ratio 3:1 (by weight); 2,6-1% by weight of DPH in the same mixture of spiropyrans; 3,4-1% by weight of DANS in the same mixture of spiropyrans.

The following description is intended to illustrate the invention and to exemplify it. It is to be construed in a non-limitative manner. The process for the preparation of the novel compounds defined above is essentially a coupling reaction of the mesogenic entity with the spiropyran entity, to result in the desired compound. Such coupling reactions, illustrated in the following Table 1, are based on the use of the respective reactive groups of these entities which can be used for such couplings.

TABLE 1

Examples of coupling reactions

TABLE 1-continued

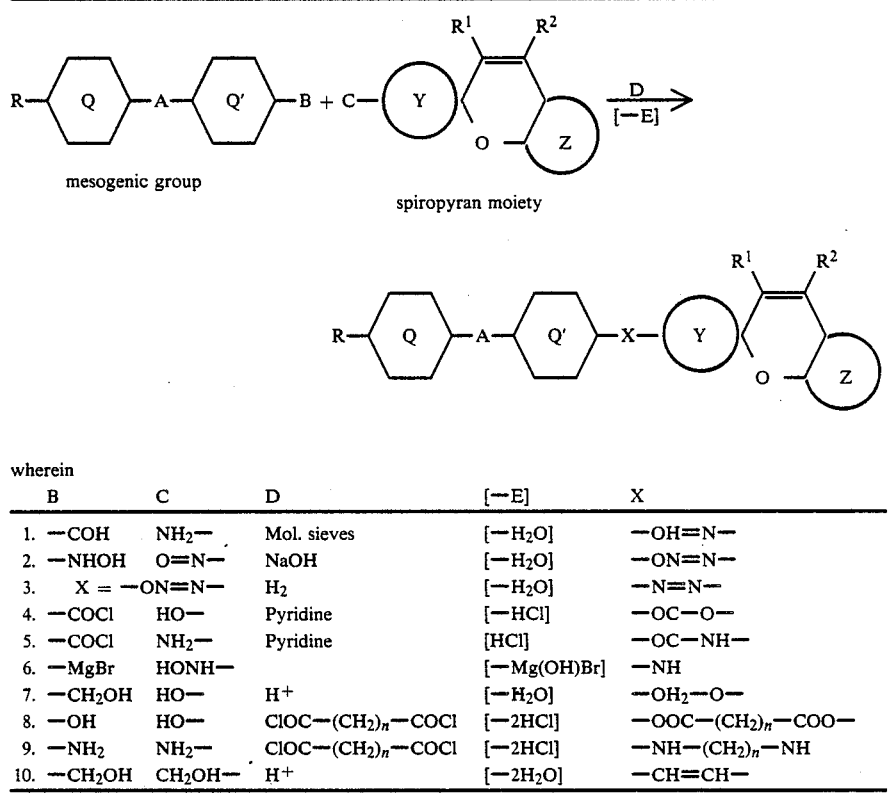

wherein

| | B | C | D | [—E] | X |
|---|---|---|---|---|---|
| 1. | —COH | NH₂— | Mol. sieves | [—H₂O] | —OH=N— |
| 2. | —NHOH | O=N— | NaOH | [—H₂O] | —ON=N— |
| 3. | X = —ON=N— | | H₂ | [—H₂O] | —N=N— |
| 4. | —COCl | HO— | Pyridine | [—HCl] | —OC—O— |
| 5. | —COCl | NH₂— | Pyridine | [HCl] | —OC—NH— |
| 6. | —MgBr | HONH— | | [—Mg(OH)Br] | —NH |
| 7. | —CH₂OH | HO— | H⁺ | [—H₂O] | —OH₂—O— |
| 8. | —OH | HO— | ClOC—(CH₂)ₙ—COCl | [—2HCl] | —OOC—(CH₂)ₙ—COO— |
| 9. | —NH₂ | NH₂— | ClOC—(CH₂)ₙ—COCl | [—2HCl] | —NH—(CH₂)ₙ—NH |
| 10. | —CH₂OH | CH₂OH— | H⁺ | [—2H₂O] | —CH=CH— |

It is stressed that it is possible to prepare a wide variety of similar compounds based on the same and analogous coupling reactions of mesogenic entities of the type illustrated for example in Kelker, H., Hatz, R., Handbook of Liquid Crystals, Chemie, Weinheim, 1980, with suitable spiropyran structures, of the type set out above and in the examples. A person versed in the art is able to produce such compounds based on the teachings of these specific examples, without any problem or difficulty as the mesogenic structures are known, or can be prepared in an analogous manner, and as the coupling reaction with the spiropyran moiety does not involve any difficulty. The surprising properties of the novel compounds makes possible a wide variety of uses, as is illustrated hereinbefore. A typical coupling reaction of this type is set out in the enclosed reaction scheme which illustrates the preparation of the spiropyran moiety and its coupling with the mesogenic group.

Properties of these novel spiropyran-merocyanine compounds are shown in the following Table 2 and full description of the procedure is given below.

Reaction scheme for preparation of the novel spiropyran-merocyanine compounds, containing mesogenic groups

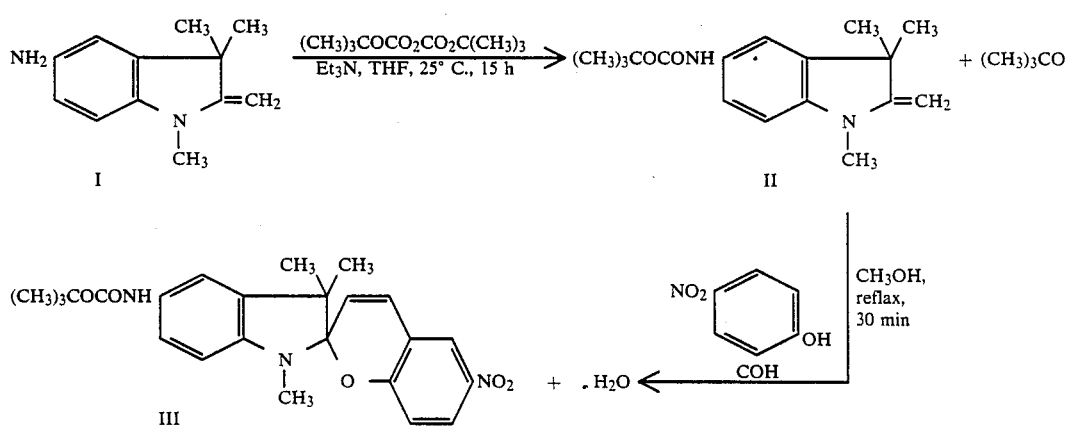

-continued

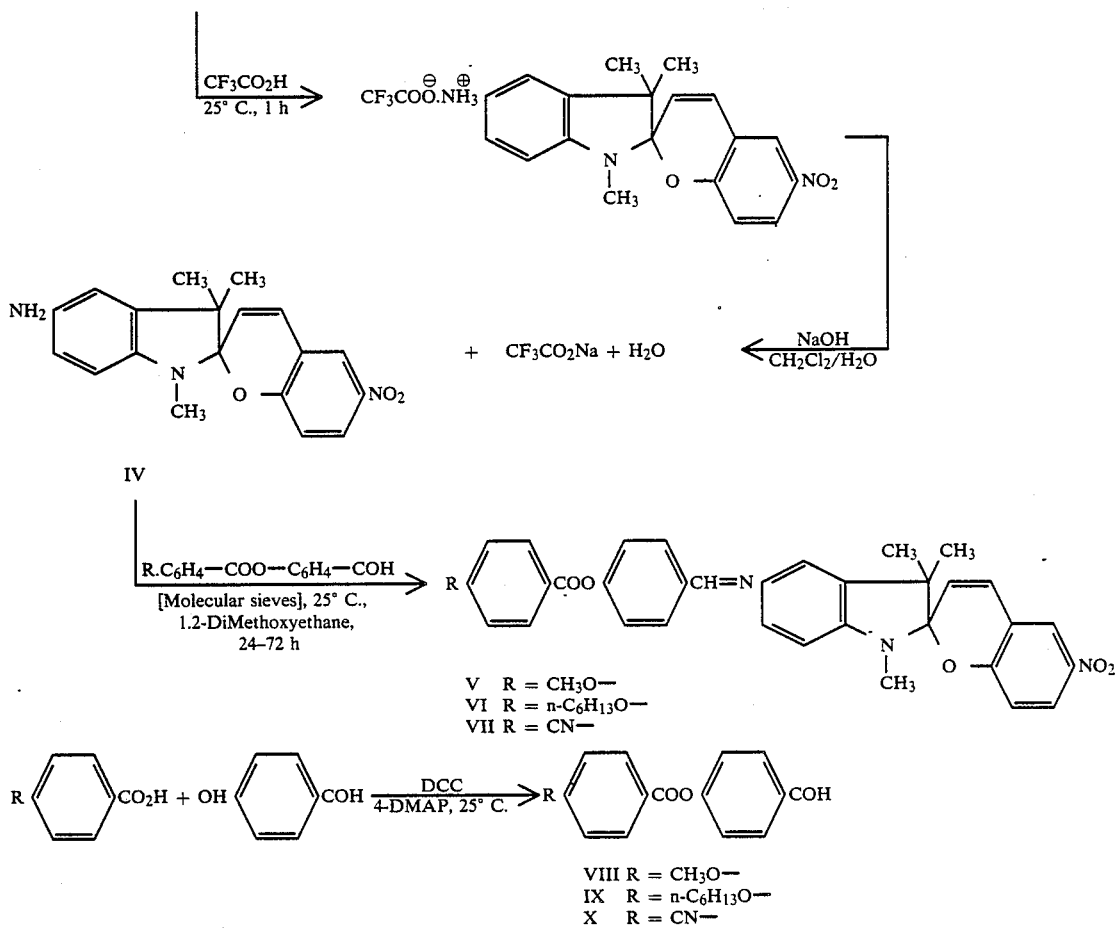

TABLE 2
Properties of novel spiropyran-merocyanine compounds containing mesogenic groups

| Compound No. | Formula | Molecular Weight | Yield % | Melting* Point, °C. | Calculated C | Calculated H | Calculated N | Found C | Found H | Found N |
|---|---|---|---|---|---|---|---|---|---|---|
| I | C$_{12}$H$_{16}$N$_2$ | 188.27 | 75 | 98–100 | 76.56 | 8.57 | 14.88 | 76.00 | 8.65 | 14.91 |
| II | C$_{17}$H$_{24}$N$_2$O$_2$ | 288.40 | 93 | R$_f$ = 0.3 Plates-DC-Aiufolien, Kieselgel 60F 254 (red spot) Eluant —CH$_3$OH:CH$_2$Cl$_2$ = 1.15 | | | | | | |
| III | C$_{24}$H$_{27}$N$_3$O$_5$ | 237.50 | 78 | 200–203 | 65.89 | 6.22 | 9.60 | 66.05 | 6.34 | 9.68 |
| IV | C$_{19}$H$_{19}$N$_3$O$_3$ | 337.38 | 55 | 148–150 | 67.64 | 5.68 | 12.45 | 67.75 | 5.61 | 12.52 |
| V | C$_{34}$H$_{29}$N$_3$O$_6$ | 575.63 | 37 | 198–203 | 70.95 | 5.08 | 7.30 | 71.06 | 5.12 | 7.35 |
| VI | C$_{39}$H$_{39}$N$_3$O$_6$ | 645.76 | 45 | 165–168 | 72.54 | 6.09 | 6.51 | 72.50 | 6.08 | 6.53 |
| VII | C$_{34}$H$_{25}$N$_4$O$_5$ | 570.60 | 48 | 210–214 | 71.57 | 4.59 | 9.82 | 71.64 | 4.60 | 9.78 |
| VIII | C$_{15}$H$_{12}$O$_4$ | 256.25 | 80 | 83–85 | 70.31 | 4.72 | | 70.33 | 4.75 | |
| IX | C$_{20}$H$_{22}$O$_4$ | 326.40 | 76 | 57–58 | 73.60 | 6.79 | | 73.58 | 6.83 | |
| X | C$_{15}$H$_9$NO$_3$ | 251.25 | 68 | 260–262 | 71.71 | 3.61 | 5.57 | 71.77 | 3.64 | 5.63 |

*not corrected

Example of preparation of spiropyran-merocyanine compounds, containing mesogenic groups 5-amino-1.3.3-trimethyl-2-methyleneindoline [amino-Fisher's base (I)] was prepared by the method described in Gale, D. J., Wilshire, J. F. K., J. Soc. Dyers Colour., 90, 97–100(1974).

5-Amino-N-tert-butyloxycarbonyl-1.3.3-trimethyl-2-methyleneindoline [BOC-amino-Fisher's base (II)] (Tarbell, D. S., Yamamoto, Y., Pope, B. M., Procl. Natl. Acad. Sci., U.S.A., 69, 730,735(1972) (Itoh, M., Hagiwara, D., Kamiya, T., Bull. Chem. Soc. Jpn., 50, 718-723(1977).

The solution of amino-Fisher's base (3.76 g, 0.02 mole), di-tert-butyldicarbonate (4.3 g, 0.02 mole) and triethulamine (TEA) (2.02 g, 0.02 mole) in 100 ml dry tetrahydrofyran (THF) which was passed through Al$_2$O$_3$/basic, was allowed to stand overnight at room temperature.

The THF and TEA were evaporated and the oily residue was dissolved in 50 ml of CH$_2$Cl$_2$. The solution was extracted (3×50 ml 5% CH$_3$COOH) to take out the BOC-amino-Fisher's base (II) in the form of its quaterney acetate salt. The water fraction with salt was washed (2×50 ml ether) and made alkaline (pH=9–10) with cooling and stirring. The white precipitate was extracted (3×50 ml CH₂Cl₂), dried with MgSO₄, filtered and then the solvent was evaporated to give 5.35 g (93%) of very viscous oil (II), rapidly becoming reddish. This product was used directly in the following step without further purification.

5-amino-N-tert-butyloxycarbonyl-1.3.3-trimethyl-6'-nitrospiro(indoline-2.2'-[2H-1] benzopyran) [BOC-amino-spiropyran(III)] (Heinnen, A., Audic, C., Gautron, R., Bull. Soc. Chim. France, 5, 2066-2074(1968).

A mixture of BOC-amino-Fischer's base (5.35 g, 0.018 m) and 5-nitrosalicylaldehyde (3.1 g, 0.018 mole) in 100 ml of methanol (analytical) was refluxed for 0.5 h. The brilliant green precipitate was separated and washed with cold methanol. After recrystallization (from hexane:benzene = 1:2) the yield of yellow crystals (III) was 6.3 g (78%).

5-amino-1.3.3 trimethyl -6'-nitrospiro (indoline-2,2'-[2H-1] benzopyran) [amino-spiropyran (IV)] (Lundt, B. F., Johansen, N. L., Volund, A., Markussen, J., Int. J. Dept. Protein Res., 12, 258,265 (19878)

BOC-amino spiropyran (6.3 g. 0.014 mole) was dissolved in 20 ml CF₃CO₂H and the solution was allowed to stand for 1 h. The yellow solution was then made alkaline (pH=11-12) with cooling and good stirring, and the brown precipitate of IV was taken up in CH₂Cl₂. The solution was washed thoroughly with water, dried with MgSO₄ and filtered, and then the solvent was evaporated. After two reprecipitations (from CH₂Cl₂/hexane) of the brown crude product, the yield of dark cherry-red crystals (IV) was 2.7 g (55%).

4-(4'-Methoxybenzoyloxy) benzaldehyde (VIII), 4-(4'-hexoxybenzoate)-benzaldehyde (IX) and 4-(4'benzonitrile) benzaldehyde (X) listed in Table 2, were synthesized by the direct room temperature esterification of the corresponding 4-methoxybenzoic acid, 4-hexoxybenzoic acid and 4-cyanobenzoic acid, respectively, with 4-hydroxybenzaldehyde, as is described in Hassner, A., Alexanian, V., Tetrahedron Letters, 46, 4475-4478(1978).

5-(4'-Methoxybenzoyloxy)-benzylidenamino-1.3.3-trimethyl 6'-nitrospiro (indoline-2.2'-[2H-1]benzopyran) (V),5-(4'hexoxybenzoate)benzylidenamino-1.3.3-trimethyl-6'-nitrospiro(indoline-2.2'-[2H-1]benzopyran) (VI) and 5-(4'benznitrile)benzylidenamino-1.3.3-trimethyl-6'nitrospiro(indoline-2.2'-[2H-1] benzopyran) (VII) were obtained by the Method A described in Orahovats, A. S., Radeva, T. Zh., Spassov, S. L., Comp. Rend. Acad. Bulg. Sci., 26,(5), 66-665(1973), in dry 1.2-dimethoxyethane as solvent, and repricipitated ferom benzene/hexane.

Example of preparation of orientated quasi-liquid crystalline films for observations of the second harmonic generation.

Solutions of spiropyrans in benzene (10 g/l) were used for film preparation. The preparation of orientated QLC film was carried out by casting a spiropyran solution onto a slide bearing vacuum-deposited electrodes, the spacing between electrodes was 1 mm. The casting was performed at a temperature of 100° C. and an electrostatic field of strength 1.5 kV/mm. The resultant films were then cooled to room temperature in the electric field. Orientated QLC films prepared in this way proved to be rigid, stable, transparent and birefringent. Characteristics of the original spiropyrans, containing mesogenic groups and quasi-liquid crystals obtained from these compounds are shown in the following Table 3.

TABLE 3

Characteristics of spiropyrans and quasi-liquid crystals

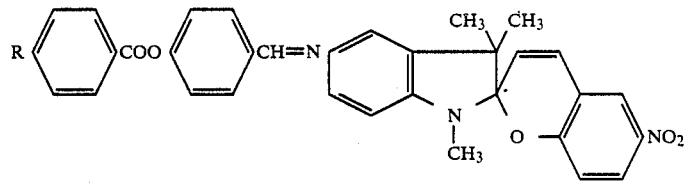

V   R = CH₃O—
VI  R = n-C₆H₁₃O—
VII R = CN—

| Compound and Mixture | Melting Point °C.* | Temperature Ranges of Phase, °C.* Amorph ⟶ QLC ⟶ Isotrop | |
|---|---|---|---|
| V | 198-203 | 50 | 130 |
| VI | 165-168 | 45 | 110 |
| VII | 210-214 | 80 | 170 |
| I:II = 3:1 | — | 50 | 135 |
| I:III = 1:1 | — | 60 | 140 |

*not corrected

The slide with the resultant quasi-liquid crystalline film was placed in the beam of a Nd³⁺/YAG laser which produced pulses of 1.06 μm light. The resulting 532 nm harmonic was detected by an EMI 9558Q photomultiplier placed behind a monochromator and Shott KG-3 filtering assembly for effectivee f/16 collection optics centered on laser beam. A 5-fold increase in detected harmonic was achieved by covering the QLC films with a low vapor pressure liquid such as dodecane or petroleum jelly (Vaseline) with a cover slip placed over this combination. This increase was interpreted as in increase both in harmonic generation and in collection efficieny.

As set out above, a wide variety of devices can be constructed which make use of the novel quasi-liquid crystal films of the present invention. Among possible use there are devices based on the ferrelectric properties of such orientated films, devices based on pyroelectric effects, devices based on piezoelectric effects and devices based on photoconductivity.

We claim:

1. A quasi-liquid crystal-forming compound of the formula:

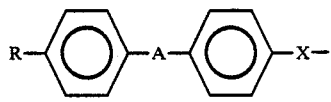

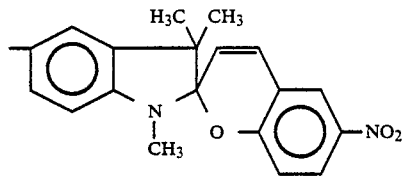

wherein,

X and A independently represent: —HC=N—; —ON=N—; —N=N—; —COO—; —HC=CH—; or —C≡C—;
R represents —OR'; —R'; —CN; —Cl; —F; —NO$_2$; —NR"$_2$; —R"; or —OR"; and
R' represents a straight chain alkyl radical and R" is a branched alkyl or alkenyl radical.

2. The compound of claim 1, wherein R represents —R'; —OR'; or —CN.

3. The compound of claim 2, wherein R represents CH$_3$O—; n—C$_6$H$_{13}$O—; or —CN.

4. The compound of claim 3, wherein A represents —HC=N—.

5. The compound of claim 3, wherein X represents —COO—.

* * * * *